(12) United States Patent
Brahem et al.

(10) Patent No.: US 11,009,474 B2
(45) Date of Patent: May 18, 2021

(54) ADAPTIVE TEST METHOD AND DESIGNS FOR LOW POWER MOX SENSOR

(71) Applicant: STMICROELECTRONICS PTE LTD, Singapore (SG)

(72) Inventors: Malek Brahem, Singapore (SG); Hatem Majeri, Aix en Provence (FR); Olivier Le Neel, Singapore (SG); Ravi Shankar, Singapore (SG)

(73) Assignee: STMICROELECTRONICS PTE LTD, Singapore (SG)

( * ) Notice: Subject to any disclaimer, the term of this patent is extended or adjusted under 35 U.S.C. 154(b) by 83 days.

(21) Appl. No.: 16/217,631

(22) Filed: Dec. 12, 2018

(65) Prior Publication Data

US 2019/0195818 A1    Jun. 27, 2019

Related U.S. Application Data

(60) Provisional application No. 62/610,459, filed on Dec. 26, 2017.

(51) Int. Cl.
*G01N 7/00* (2006.01)
*G01N 21/00* (2006.01)
(Continued)

(52) U.S. Cl.
CPC ......... *G01N 27/123* (2013.01); *G01N 27/125* (2013.01); *G01N 33/0031* (2013.01);
(Continued)

(58) Field of Classification Search
CPC ............... G01N 27/123; G01N 27/125; G01N 33/0031; G01N 33/0047; G01N 7/00;
(Continued)

(56) References Cited

U.S. PATENT DOCUMENTS

| | | |
|---|---|---|
| 9,448,198 B2 | 9/2016 | Le Neel et al. |
| 9,459,224 B1 | 10/2016 | Cheng et al. |
| | (Continued) | |

FOREIGN PATENT DOCUMENTS

| | | |
|---|---|---|
| CN | 101932923 A | 12/2010 |
| CN | 102890107 A | 1/2013 |
| | (Continued) | |

OTHER PUBLICATIONS

Bochenkov et al., "Chapter 2: Sensitivity, Selectivity, and Stability of Gas-Sensitive Metal-Oxide Nanostructures," *Laboratory of Low Temperature Chemistry, Department of Chemistry, M. V. Lomonosov Moscow State University*, Moscow, Russia, © 2010, 22 pages.

*Primary Examiner* — Brian J. Sines
(74) *Attorney, Agent, or Firm* — Seed IP Law Group LLP (57) ABSTRACT

The present disclosure is directed to a gas sensor device that includes a plurality of gas sensors. Each of the gas sensors includes a semiconductor metal oxide (SMO) film, a heater, and a temperature sensor. Each of the SMO films is designed to be sensitive to a different gas concentration range. As a result, the gas sensor device is able to obtain accurate readings for a wide range of gas concentration levels. In addition, the gas sensors are selectively activated and deactivated based on a current gas concentration detected by the gas sensor device. Thus, the gas sensor device is able to conserve power as gas sensors are on when appropriate instead of being continuously on.

20 Claims, 9 Drawing Sheets

(51) Int. Cl.
*G01N 27/00* (2006.01)
*G01N 31/00* (2006.01)
*G01N 33/00* (2006.01)
*G01N 27/12* (2006.01)

(52) U.S. Cl.
CPC ..... *G01N 33/0047* (2013.01); *G01N 33/0065* (2013.01); *G01N 33/0075* (2013.01)

(58) Field of Classification Search
CPC ........ G01N 21/00; G01N 27/00; G01N 31/00; G01N 33/00
See application file for complete search history.

(56) References Cited

U.S. PATENT DOCUMENTS

| | | | | |
|---|---|---|---|---|
| 2002/0142477 | A1* | 10/2002 | Lewis | G01N 33/0031 436/151 |
| 2006/0042353 | A1 | 3/2006 | Marquis et al. | |
| 2006/0240245 | A1* | 10/2006 | Ishida | G01N 27/12 428/312.6 |
| 2010/0116068 | A1 | 5/2010 | Oki et al. | |
| 2014/0260546 | A1* | 9/2014 | Chen | G01N 27/12 73/31.06 |
| 2016/0018356 | A1* | 1/2016 | Shankar | G01N 27/12 205/775 |
| 2016/0334359 | A1* | 11/2016 | Kim | C01G 49/02 |
| 2017/0102353 | A1* | 4/2017 | Lei | G01N 27/128 |
| 2018/0017513 | A1* | 1/2018 | Le Neel | G01N 27/128 |
| 2019/0257804 | A1* | 8/2019 | Brahem | G01N 27/12 |

FOREIGN PATENT DOCUMENTS

| | | |
|---|---|---|
| CN | 104034759 A | 9/2014 |
| CN | 105319245 A | 2/2016 |
| CN | 205139071 U | 4/2016 |
| CN | 106324038 A | 1/2017 |
| WO | 2016/105012 A1 | 6/2016 |

* cited by examiner

ADAPTIVE TEST METHOD AND DESIGNS FOR LOW POWER MOX SENSOR

BACKGROUND

Technical Field

The present disclosure is directed to a gas sensor device to detect air quality.

Description of the Related Art

Air quality is important to maintain one's health. Air pollution may lead to a variety of health issues, such as cardiopulmonary ailments. Air pollution is not limited to outdoor pollution, and may occur indoors, such as in homes, offices, and factories. A large range of chemical compounds, such as volatile organic compounds (VOC), can be found in indoor environments. VOCs include compounds, such as ethanol, toluene, benzene, formaldehyde, tetrachloroethene (TCE), and methylene chloride.

Indoor air pollution may derive from a wide variety of different sources, such as air conditioners, building materials, furniture, solvents, paint, and carpeting. Indoor air pollution may even be caused by quotidian activities, such a breathing, cooking, and cleaning.

As stale air accumulates within an enclosed space, concentrations of VOCs may rise to harmful levels. In some cases, indoor air pollution is a larger health hazard than outdoor air pollution.

Some people are particularly sensitive to VOCs and will experience allergic reactions, such as headaches, dizziness, and irritation. However, most people are unable to detect hazardous levels of VOCs. Accordingly, it is important for buildings to be equipped with gas sensors to detect harmful levels of gases, such as VOCs, to maintain proper air quality.

BRIEF SUMMARY

The present disclosure is directed to an improved gas sensor device for detecting air quality. The gas sensor device may be used for a variety of applications, such as an indoor air quality sensor and an outdoor air quality sensor. The gas sensor device is able to make accurate readings for a wide range of gas concentration levels. In addition, the gas sensor device has low power consumption, which makes it ideal for low power devices, such as smart phones and smart watches.

The gas sensor device includes a plurality of gas sensors. Each of the gas sensors includes a semiconductor metal oxide (SMO) film, a heater, and a temperature sensor. Each of the SMO films is designed to be sensitive to a different gas concentration range. For example, a first SMO film may be designed to detect a low gas concentration range, a second SMO film may be designed to detect a mid gas concentration range, and a third SMO film may designed to detect a high gas concentration range. By having each of the SMO films being sensitive to a different gas concentration range, the gas sensor device is able to obtain accurate readings for a wide range of gas concentration levels.

The gas sensor device selectively activates and deactivates the gas sensors based on a current gas concentration detected by the gas sensor device. For example, when a low gas concentration is detected, the gas sensor device may activate a gas sensor with an SMO film designed to detect a low gas concentration range, and deactivate all other gas sensors. As a result, the gas sensor device conserves power, as gas sensors are turned on when appropriate instead of being continuously on.

BRIEF DESCRIPTION OF THE SEVERAL VIEWS OF THE DRAWINGS

In the drawings, identical reference numbers identify similar features or elements. The size and relative positions of features in the drawings are not necessarily drawn to scale.

DETAILED DESCRIPTION

In the following description, certain specific details are set forth in order to provide a thorough understanding of various aspects of the disclosed subject matter. However, the disclosed subject matter may be practiced without these specific details. In some instances, well-known structures and methods of manufacturing electronic devices have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting or glass substrates, whether or not the components are coupled together into a circuit or able to be interconnected. Throughout the specification, the term "layer" is used in its broadest sense to include a thin film, a cap, or the like, and one layer may be composed of multiple sub-layers.

The present disclosure is directed to a gas sensor device that detects various species of gas including volatile organic compounds (VOC). The gas sensor device is able to obtain accurate readings for a wide range of concentration levels. Further, the gas sensor device has low power consumption and is ideal for portable devices, such as smart phones and smart watches.

Figure 1:
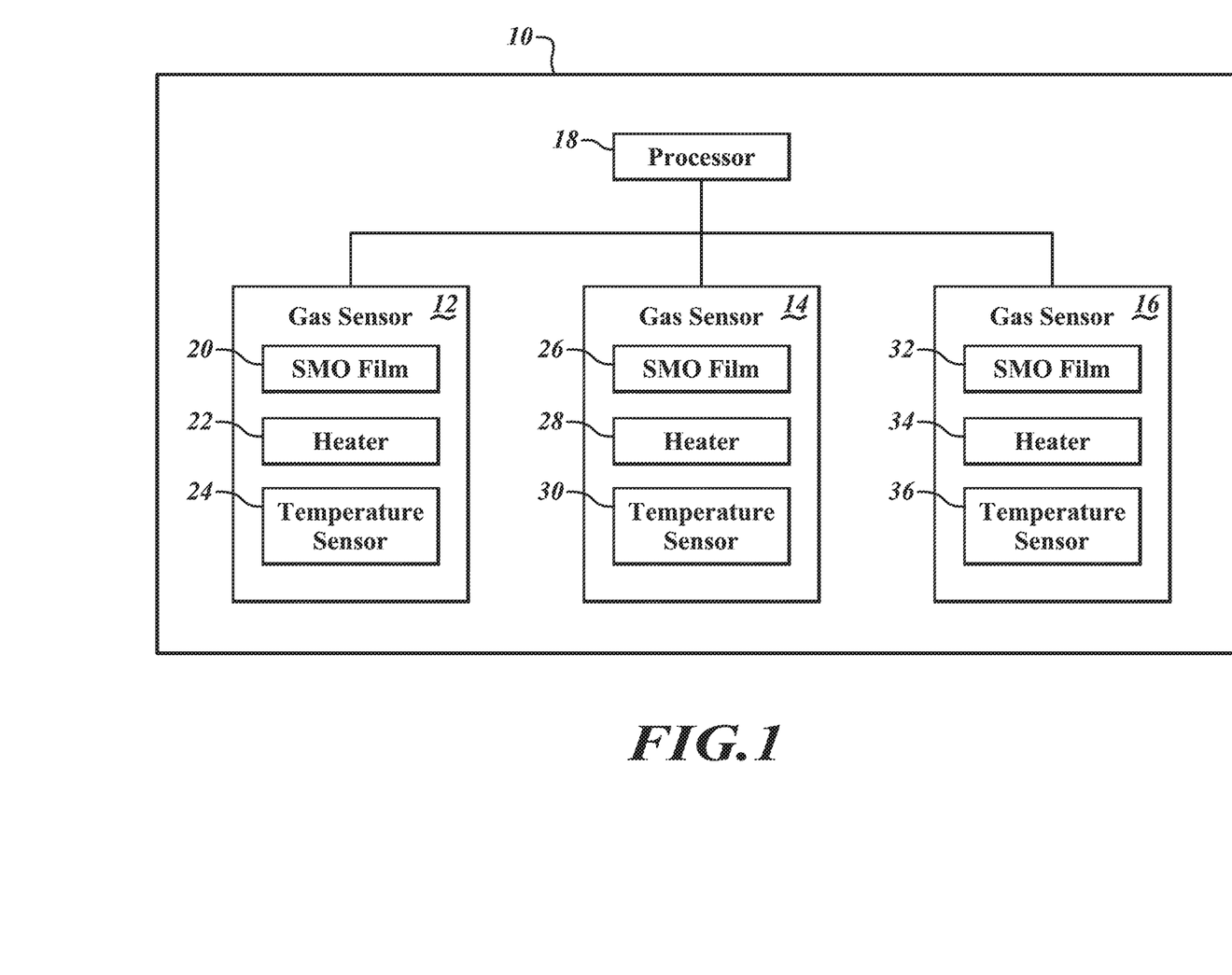
FIG. 1 is a block diagram of a gas sensor device according to an embodiment of the present disclosure.

FIG. 1 is a block diagram of a gas sensor device 10 according to one embodiment of the present disclosure. The gas sensor device 10 includes a plurality of gas sensors 12, 14, 16, and a processor 18. Although only three gas sensors are shown in FIG. 1, the gas sensor device 10 may include any number of gas sensors.

Each of the gas sensors 12, 14, 16 is configured to detect a species of gas, such as a volatile organic compound (VOC). Each of the gas sensors 12, 14, 16 includes a semiconductor metal oxide (SMO) film, a heater, and a temperature sensor. In particular, the gas sensor 12 includes an SMO film 20, a heater 22, and a temperature sensor 24; the gas sensor 14 includes an SMO film 26, a heater 28, and a temperature sensor 30; and the gas sensor 16 includes an SMO film 32, a heater 34, and a temperature sensor 36.

Each of the SMO films 20, 26, 32 is a material that chemically reacts with various gases in a surrounding environment. For example, the SMO film 20 may include tin oxide ($SnO_2$), zinc oxide ($ZnO_2$), and/or indium oxide ($In_2O_3$). Each of the SMO films 20, 26, 32 acts as an active sensor area. When heated to certain temperatures, the SMO films 20, 26, 32 experience a change in resistivity when exposed to certain gases. For example, when heated to between 100 to 400 degrees Celsius, a resistance of a film of tin oxide changes in the presence of methane gas ($CH_4$), liquid petroleum gas (LPG), or hydrogen gas ($H_2$). Accordingly, a presence of a specific gas may be detected based on a current resistivity of the SMO films 20, 26, 32.

In one embodiment, each of the SMO films 20, 26, 32 is a thin film. For example, each of the SMO films 20, 26, 32 may be between 90 to 110 nanometers (nm) thick.

A sensitivity level of the SMO films 20, 26, 32 for a particular concentration range of gas is determined by the design of the SMO films 20, 26, 32. In general, the concentration range of gas in which an SMO film will be sensitive to is determined by the number of oxygen sites available on the SMO film to react with gas molecules. When all of the oxygen sites of an SMO film are occupied by active gas molecules, the SMO film will saturate and will not be as sensitive to any additional gas molecules present. Thus, an SMO film having a large surface area film will be able to detect higher concentrations of the gas, as the SMO film has a larger number of oxygen sites available to react with gas molecules. Conversely, when a large number of the oxygen sites of an SMO film are left unoccupied, the SMO film will be less reactive and undergo smaller changes in the presence of a gas. Thus, an SMO film having a large surface is generally insensitive to low concentrations of gas, as the SMO film will have a large number of unoccupied oxygen sites.

Accordingly, the size or surface area of each of the SMO films 20, 26, 32 determine the gas concentration range in which each of the SMO films 20, 26, 32 will be sensitive to. SMO films with large exposed surface areas are generally more sensitive to high concentrations of gases and less sensitive to low concentrations of gases. SMO films with small exposed surface areas are generally less sensitive to high concentrations of gases and more sensitive to low concentrations of gases.

Figure 2:
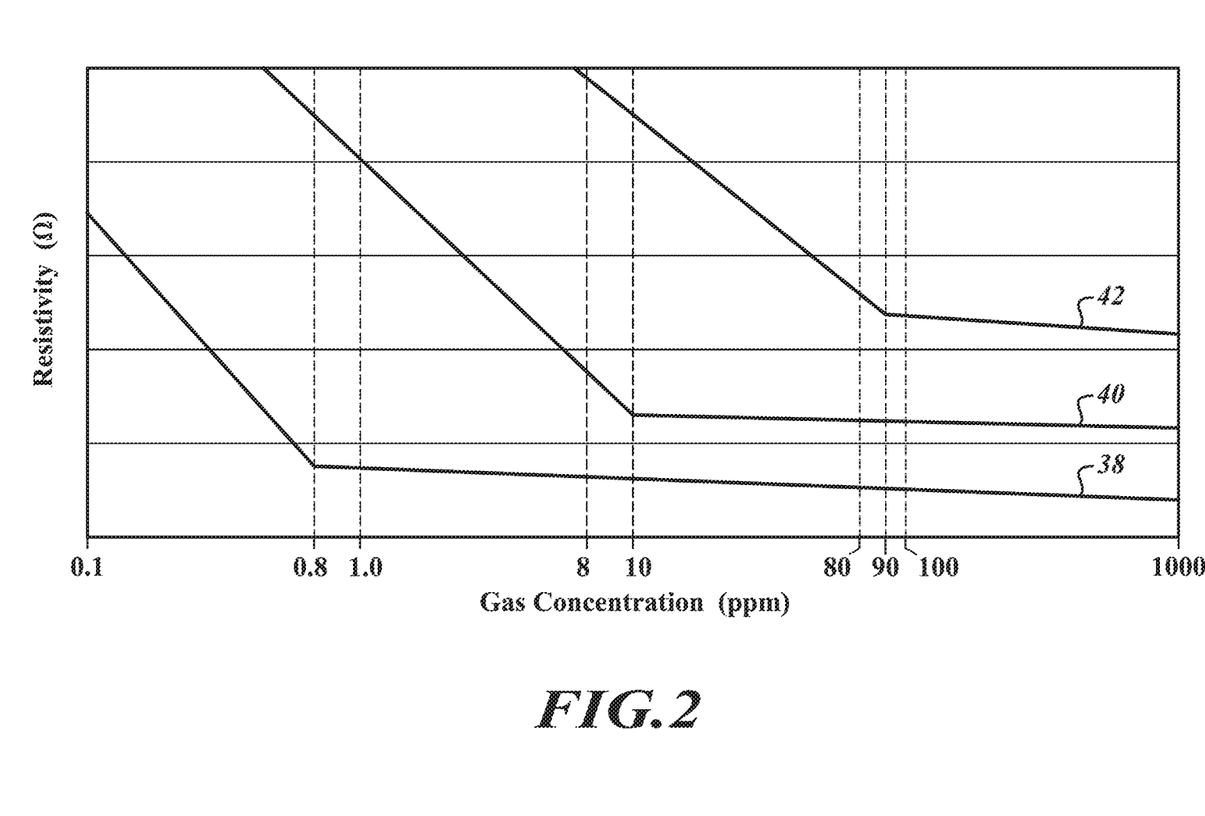
FIG. 2 is a graph of sensitivities for three different SMO films according to an embodiment of the present disclosure.

For example, an SMO film having a surface area of 10 micrometers squared ($\mu m^2$) reacts well and is sensitive to gas concentrations in the range of 1 part per billion (PPB) to 1 PPM, an SMO film having a surface area of 100 $\mu m^2$ reacts well and is sensitive to gas concentrations in the range of 1 PPM to 10 PPM; and an SMO film having a surface area of 1000 $\mu m^2$ reacts well and is sensitive to gas concentrations in the range of 10 PPM to 100 PPM. FIG. 2 is a graph of sensitivities for three different SMO films, according to an embodiment of the present disclosure. Line 38 represents a response of an SMO film having a surface area of 10 $\mu m^2$, line 40 represents a response of an SMO film having a surface area of 100 $\mu m^2$, and line 42 represents a response of an SMO film having a surface area of 1000 $\mu m^2$.

The line 38 shows that the SMO film having a surface area of 10 $\mu m^2$ has a greater rate of change (i.e., slope) of resistivity for gas concentrations less than 0.8 PPM than for gas concentrations greater than 0.8 PPM. Thus, the SMO film having a surface area of 10 $\mu m^2$ is particularly sensitive to gas concentrations up to approximately 0.8 PPM. The line 40 shows that the SMO film having a surface area of 100 $\mu m^2$ has a greater rate of change of resistivity for gas concentrations less than 10 PPM than for gas concentrations greater than 10 PPM. Thus, the SMO film having a surface area of 100 $\mu m^2$ is particularly sensitive to gas concentrations up to approximately 10 PPM. The line 42 shows that the SMO film having a surface area of 1000 $\mu m^2$ has a greater rate of change of resistivity for gas concentrations less than 90 PPM than for gas concentrations greater than 90 PPM. Thus, the SMO film having a surface area of 100 $\mu m^2$ is particularly sensitive to gas concentrations up to approximately 90 PPM. Each of the SMO films 20, 26, 32 is designed to be sensitive to a different gas concentration range. Namely, each of the SMO films 20, 26, 32 has a different exposed surface area such that each of the SMO films 20, 26, 32 is sensitive to a different gas concentration range. By having each of the SMO films 20, 26, 32 being sensitive to a different concentration range, the gas sensors 12, 14, 16 are able to obtain accurate readings for a wide range of gas concentration levels.

In one embodiment, the SMO film 20 has a first surface area in order to detect a low gas concentration range, the SMO film 26 has a second surface area that is larger than the first surface area in order to detect a mid gas concentration range, and the SMO film 32 has a third surface area that is larger than the second surface area in order to detect a high gas concentration range. For example, in one embodiment, the SMO film 20 has a surface area approximately equal to 10 $\mu m^2$, the SMO film 26 has a surface area approximately equal to 100 $\mu m^2$, and the SMO film 32 has a surface area approximately equal to 1000 $\mu m^2$. Thus, the gas sensor 12 is able to detect gas concentrations in the range of 1 PPB to 1 PPM, the gas sensor 14 is able to detect gas concentrations in the range of 1 PPM to 10 PPM; and the gas sensor 16 is able to detect gas concentrations in the range of 10 PPM to 100 PPM. Accordingly, the gas sensor device 10 is able to accurately detect and measure gas concentrations in the range of 0 to 100 PPM.

The heaters 22, 28, 34 heat the SMO films 20, 26, 32, respectively, to a desired temperature. In one embodiment, the heaters 22, 28, 34 are resistive heaters that heat the SMO films 20, 26, 32 using the Joule effect, by dissipating current through a resistance. As will be discussed in further detail with respect to FIGS. 3-5, the heaters 22, 28, 34 underlie and heat the SMO films 20, 26, 32, respectively.

As previously discussed, the SMO films 20, 26, 32 should be heated to a specific temperature in order to react with a specific gas. In one embodiment, the heaters 22, 28, 34 heat the SMO films 20, 26, 32, respectively, to be within the same temperature range in order to sense the same gas.

The power consumption of the heaters 22, 28, 34 to heat the SMO films 20, 26, 32 depend on the size of the SMO films 20, 26, 32. Generally, the larger the SMO film is, the more power is needed to heat the SMO film to a desired temperature. For example, if the SMO films 20, 26, 32 have surface areas approximately equal to 10 $\mu m^2$, 100 $\mu m^2$, and 1000 $\mu m^2$, respectively, the heaters 22, 28, 34 will consume approximately 5 milliwatts (mW), 15 mW, and 35 mW, respectively, to heat the SMO films 20, 26, 32 to be between 300 to 350 degrees Celsius. As will be discussed in further detail with respect to FIG. 8, the heaters 22, 28, 34 are selectively activated and deactivated to conserve power.

The temperature sensors 24, 30, 36 measure the current temperature of the SMO films 20, 26, 32, respectively. The temperature sensors 24, 30, 36 are positioned adjacent to the SMO films 20, 26, 32, respectively, in order to obtain accurate measurements. As will be discussed in further detail below, the temperature sensors 24, 30, 36 are used as a feedback control device for automatically adjusting the heaters 22, 28, 34, respectively, to heat the SMO films 20, 26, 32 to desired temperatures. For example, the temperature sensor 24 may measure a current temperature of the SMO film 20, and the heater 22 may adjust its temperature based on the current temperature of the SMO film 20.

The processor 18 is coupled to the gas sensors 12, 14, 16. The processor 18 is configured to activate and deactivate each of the gas sensors 12, 14, 16; measure current resistivity of the SMO films 20, 26, 32; control the heaters 22, 28, 34 to heat the SMO films 20, 26, 32 to a particular temperature; and communicate with the temperature sensors 24, 30, 36 to obtain current temperatures of the SMO films 20, 26, 32. The processor 18 may be any type of controller, microprocessor, or application specific integrated circuit (ASIC) that communicates with and controls the gas sensors 12, 14, 16.

In one embodiment, the processor 18 reads the current temperatures of the SMO films 20, 26, 32 via the temperature sensors 24, 30, 36, respectively; and then controls the heaters 22, 28, 34 based on the current temperature of the SMO films 20, 26, 32, respectively. For example, the processor 18 may receive the current temperature of the SMO film 20 via the temperature sensor 24, and adjust the heater 22 to maintain a desired temperature (e.g., between 300 to 350 degrees Celsius) of the SMO film 20. By adjusting the heaters 22, 28, 34 to specific temperatures, the processor 18 is able to tune the gas sensors 12, 14, 16, more specifically the SMO films 20, 26, 32, to be sensitive to a particular gas. In one embodiment, the processors 18 adjust the heaters 22, 28, 34 to maintain the same temperature range such that the SMO films 20, 26, 32 are sensitive to the same gas.

In one embodiment, the processor 18 activates and deactivates each of the gas sensors 12, 14, 16 to conserve power. As previously discussed, the larger the SMO film is, the more power is needed to heat the SMO film to a desired temperature. Thus, in order to conserve power, the processor 18 activates and deactivates the gas sensors 12, 14, 16 depending on which of the gas sensors 12, 14, 16 is the most sensitive to a gas concentration range currently present in a surrounding environment. As a result, gas sensors with larger SMO films and large power consumptions are not powered when not in use. The activation and deactivation of the gas sensors 12, 14, 16 will be discussed in further detail with respect to FIG. 8.

Figure 3:
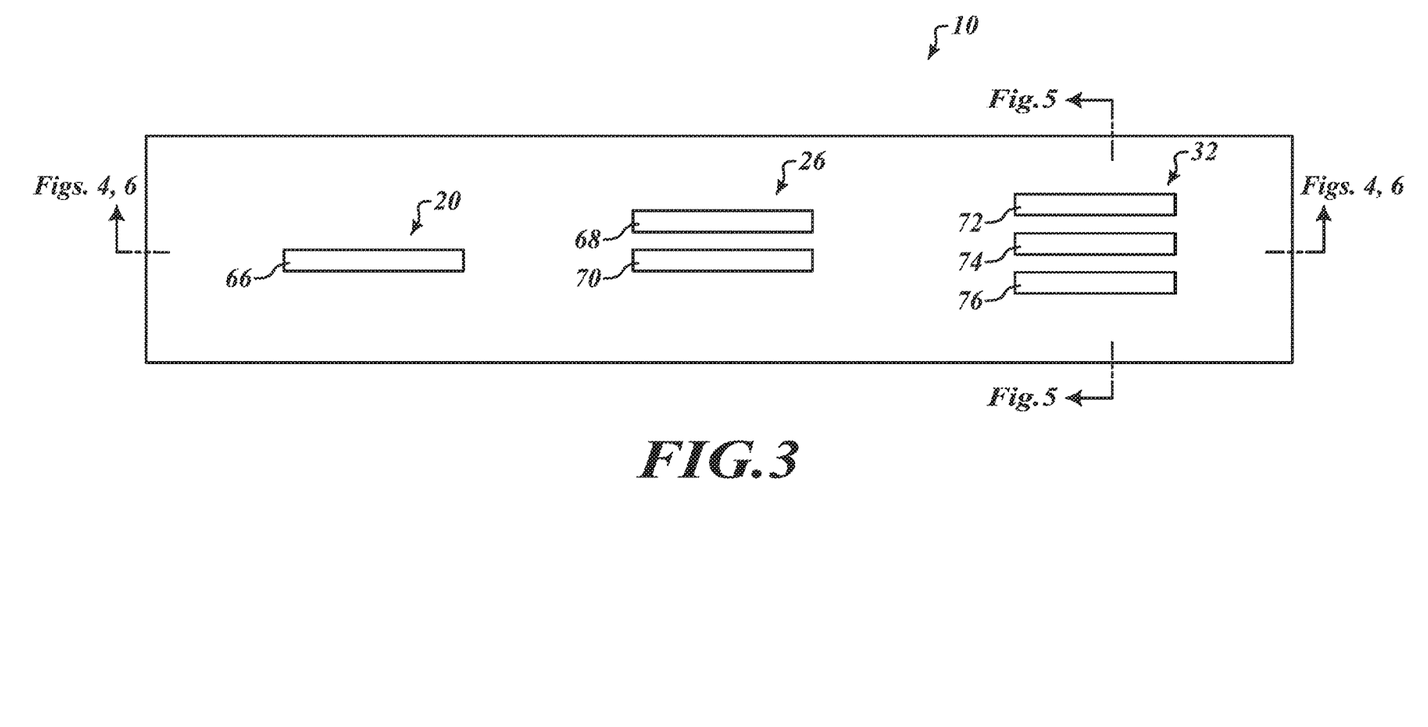
FIG. 3 is a top view of the gas sensor device according to an embodiment of the present disclosure.
Figure 4:
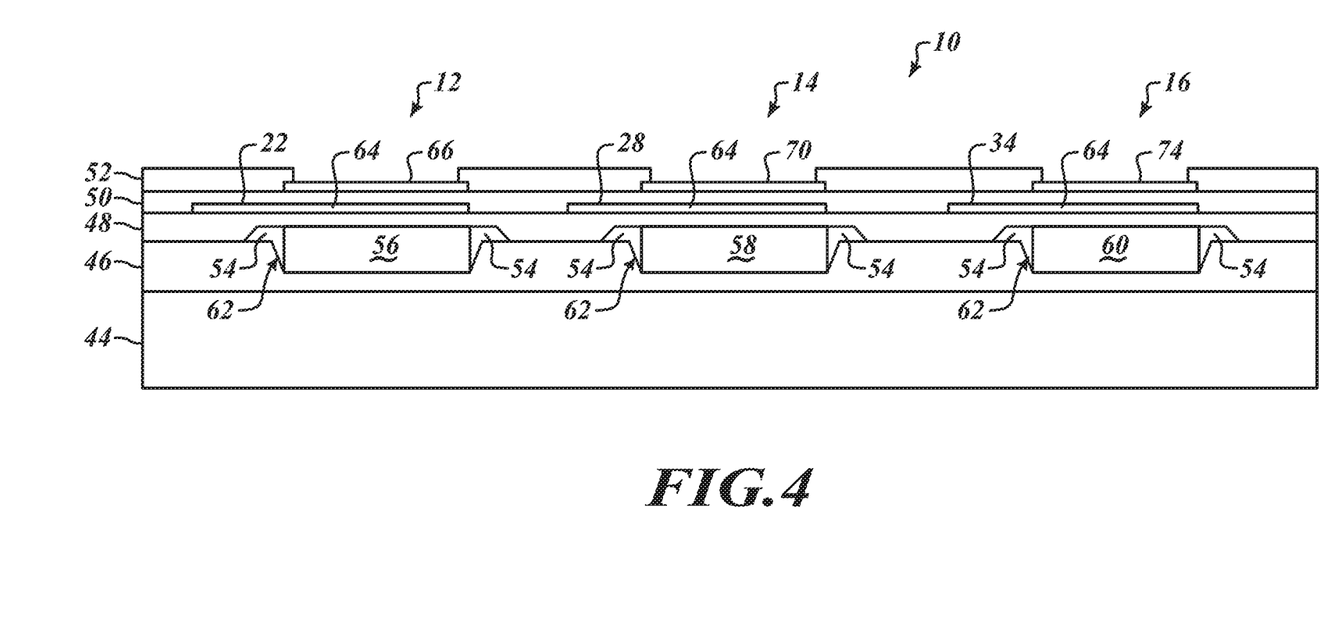
FIG. 4 is a cross-sectional view of the gas sensor device along the axis shown in FIG. 3 according to an embodiment of the present disclosure.
Figure 5:
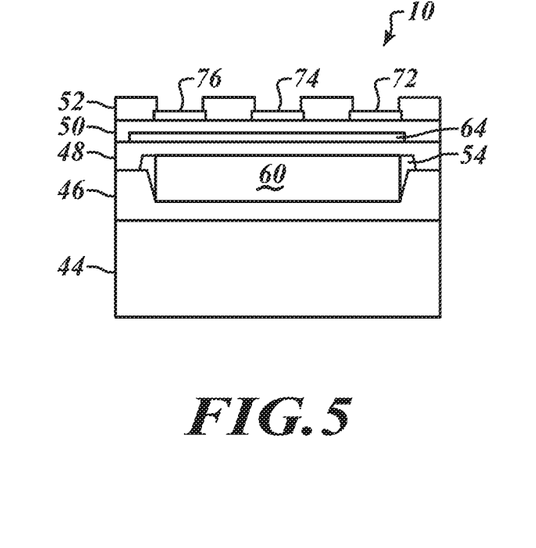
FIG. 5 is a cross-sectional view of the gas sensor device along the axis shown in FIG. 3 according to an embodiment of the present disclosure.

FIG. 3 is a top view of the gas sensor device according to an embodiment of the present disclosure. FIG. 4 is a cross-sectional view of the gas sensor device along the axis shown in FIG. 3 according to an embodiment of the present disclosure. FIG. 5 is a cross-sectional view of the gas sensor device along the axis shown in FIG. 3 according to an embodiment of the present disclosure. It is beneficial to review FIGS. 3 to 5 together. It is noted that the dimensions set forth herein are provided as examples. Other dimensions are envisioned for this embodiment and all other embodiments of this application. The gas sensor device 10 includes the SMO films 20, 26, 32; the heaters 22, 28, 34; a substrate 44; a first dielectric layer 46; a second dielectric layer 48; a third dielectric layer 50; and a fourth dielectric layer 52.

The first dielectric layer 46 is formed on the substrate 44 using, for example, deposition or a growth process. The substrate 44 may be made of, for example, silicon or glass. In one embodiment, the substrate 44 has a thickness in the range of 500 to 600 $\mu m$ thick. The first dielectric layer 46 may be made of, for example, oxide. In one embodiment, the first dielectric layer 46 has a thickness in the range of 3 to 10 $\mu m$.

The second dielectric layer 48 is formed on the first dielectric layer 46 using, for example, deposition or a growth process. The second dielectric layer 48 may be made of, for example, silicon nitride. In one embodiment, the second dielectric layer 46 has a thickness in the range of 300 to 550 nm.

Cavities 56, 58, 60 are formed between the first dielectric layer 46 and the second dielectric layer 48. As best shown in FIG. 4, each of the gas sensors 12, 14, 16 includes a respective cavity. Namely, the gas sensor 12 includes the cavity 56, the gas sensor 14 includes the cavity 58, and the gas sensor 16 includes the cavity 60. The cavities 56, 58, 60 may be formed by patterning recesses 62 in the first dielectric layer 46 using, for example, photolithography and etching techniques; and filling the recesses 62 with a sacrificial material 54, such as polyimide. The second dielectric layer 48 may then be formed on the first dielectric layer 46 and the polyimide 54. Portions of the polyimide 54 may then be removed using, for example, photolithography and etching techniques. Remaining portions of the polyimide 54, as best shown in FIG. 4, provide additional support for portions of the second dielectric layer 48 overlying the cavities 56, 58, 60. In one embodiment, each of the cavities 56, 58, 60 has a depth in the range of 2 to 5 $\mu m$.

The cavities 56, 58, 60 provide air gaps between the first dielectric layer 46 and the second dielectric layer 48. As air has low thermal conductivity, the cavities 56, 58, 60 provide thermal insulation and confine heat within the gas sensors 12, 14, 16. As a result, temperatures of the SMO films 20, 26, 32 may be maintained with less power. In addition, as polyimide also has low thermal conductivity, the polyimide 54 provides additional thermal insulation for the gas sensors 12, 14, 16.

The heaters 22, 28, 34 are formed on the second dielectric layer 48 using, for example, deposition. The heaters 22, 28, 34 directly overlie the cavities 56, 58, 60, respectively. As previously discussed, in one embodiment, the heaters 22, 28, 34 are resistive heaters that heat the SMO films 20, 26, 32 using the Joule effect by dissipating current through a resistance. In this embodiment, the heaters 22, 28, 34 include a resistive layer 64, such as tantalum aluminum. In one embodiment, the resistive layer 64 has a thickness in the range of 100 to 200 nm. Although a single resistive layer is shown in FIG. 4, the heaters 22, 28, 34 may include a plurality of resistive layers. In one embodiment, the heaters 22, 28, 34 include at least one resistive layer on both sides of the SMO films 20, 26, 32 such that at least a portion of the SMO films 20, 26, 32 are sandwiched between two resistive layers.

The third dielectric layer 50 is formed on the second dielectric layer 48 and the heaters 22, 28, 34 using, for example, deposition or a growth process. The third dielectric layer 50 may be made of, for example, silicon nitride. In one embodiment, the third dielectric layer 50 has a thickness in the range of 200 to 400 nm.

The SMO films 20, 26, 32 are formed on the third dielectric layer 50 using, for example, deposition. The SMO films 20, 26, 32 may be formed by forming an SMO layer on the third dielectric layer 50 and patterning the SMO layer using, for example, photolithography and etching techniques. As previously discussed, the SMO films 20, 26, 32 are made of a materials that chemically reacts with various gases in a surrounding environment. For example, the SMO layer may include tin oxide ($SnO_2$), zinc oxide ($ZnO_2$), and/or indium oxide ($In_2O_3$). In one embodiment, the SMO layer (i.e., each of the SMO films 20, 26, 32) has a thickness in the range of 50 to 150 nm.

As best shown in FIG. 3, each of the SMO films 20, 26, 32 has a different upper surface area such that each of the SMO films 20, 26, 32 is sensitive to a different gas concentration range. In particular, the SMO film 20 has an exposed upper surface having first surface area, the SMO film 26 has an exposed upper surface having second surface area that is larger than the first surface area, and the SMO film 32 has an exposed upper surface having a third surface area that is larger than the second surface area. Accordingly, each of the SMO films 20, 26, 32 is sensitive to a different gas concentration range.

In one embodiment, each of the SMO films 20, 26, 32 includes one or more SMO segments. For example, as shown in FIG. 3, the SMO film 20 include a single SMO segment 66, the SMO film 26 includes two separate SMO segment 68, 70, and the SMO film 32 includes three separate SMO segments 72, 74, 76. In one embodiment, each of the SMO segments has the same surface area.

As previously discussed, in one embodiment, the SMO film 20 has a first surface area, the SMO film 26 has a second surface area that is larger than the first surface area, and the SMO film 32 has a third surface area that is larger than the second surface area. In this embodiment, the first surface area is the exposed surface area of the SMO segment 66, the second surface area is the combined exposed surface areas of the SMO segment 68, 70, and the third surface area is the combined exposed surface areas of the SMO segments 72, 74, 76.

A fourth dielectric layer 52 is formed on the third dielectric layer 50 and the SMO films 20, 26, 32 using, for example, deposition or a growth process. The fourth dielectric layer 52 is patterned using, for example, photolithography and etching techniques to expose the SMO films 20, 26, 32 such that the SMO films 20, 26, 32 are exposed to a surrounding environment, as shown in FIG. 3. The fourth dielectric layer 52 may be made of, for example, silicon nitride. In one embodiment, the fourth dielectric layer 52 has a thickness in the range of 300 to 550 nm.

In the embodiment shown in FIGS. 3 to 6, the gas sensors 12, 14, 16 are all formed on the same die. Namely, the gas sensors 12, 14, 16 are formed on the substrate 44. However, the gas sensors 12, 14, 16 may also be formed on separate dies.

It is noted that the processor 18 and the temperature sensors 24, 30, 36 are not shown in FIGS. 3 to 5 for simplicity purposes. In one embodiment, the gas sensors 14, 16, 18 and the processor 18 are all formed on the same substrate. In one embodiment, the processor 18 is formed on a separate substrate from the gas sensors 12, 14, 16, and is electrically coupled to the gas sensors 12, 14, 16 via an interconnect. In one embodiment, the temperature sensors 24, 30, 36 are positioned adjacent to the SMO films 20, 26, 32, respectively, in order to obtain accurate measurements. In addition, although not shown in FIGS. 3 to 5, the gas sensor device 10 may include a plurality of conductive layers that electrically couple the SMO films 20, 26, 32 and the heaters 22, 28, 34 to the processor 18 and/or other electrical components.

Figure 6:
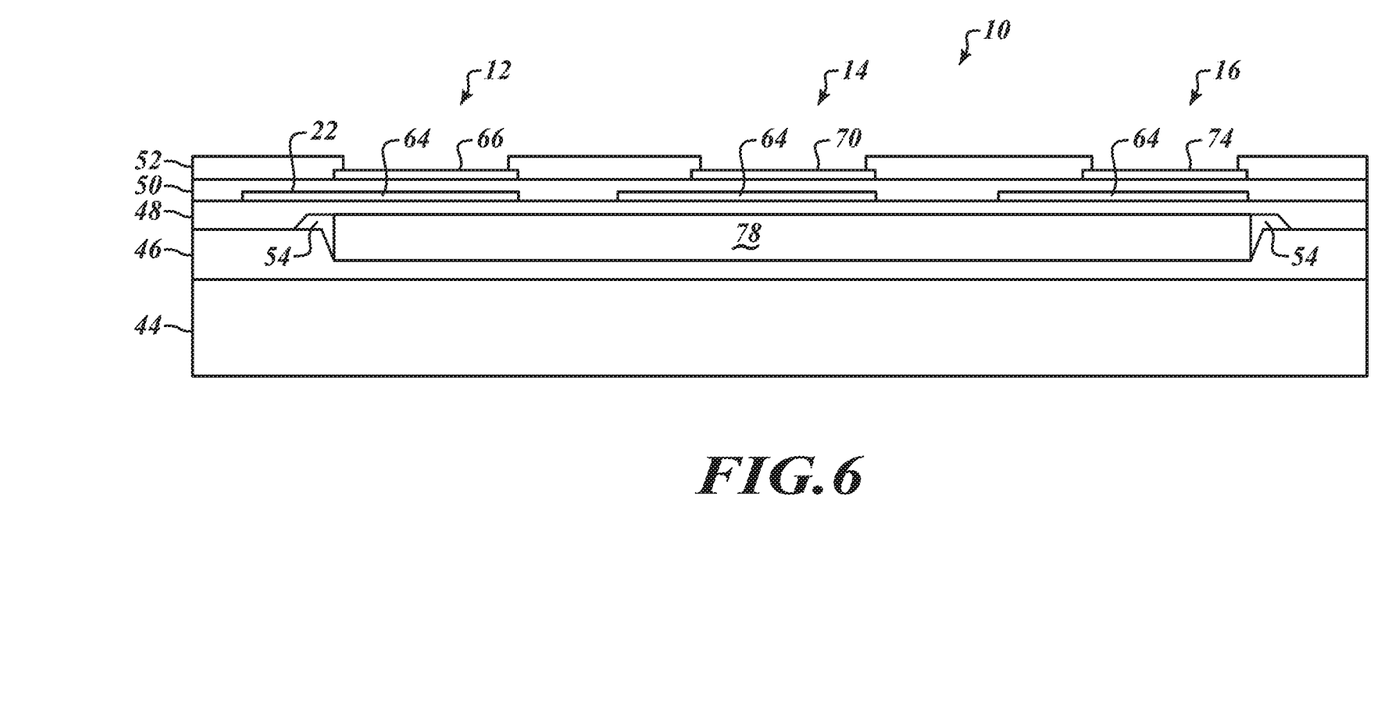
FIG. 6 is a cross-sectional view of the gas sensor device along the axis shown in FIG. 3 according to another embodiment of the present disclosure.

FIG. 6 is a cross-sectional view of the gas sensor device along the axis shown in FIG. 3 according to another embodiment of the present disclosure.

In the embodiment shown in FIG. 4, each of the gas sensors 12, 14, 16 includes a respective cavity. That is, the gas sensor 12 includes the cavity 56, the gas sensor 14 includes the cavity 58, and the gas sensor 16 includes the cavity 60. In contrast, in the embodiment shown in FIG. 6, the gas sensors 12, 14, 16 share a single cavity 78. Similar to the cavities 56, 58, 60, the cavity 78 provide an air gap between the first dielectric layer 46 and the second dielectric layer 48 to provide thermal insulation for the gas sensors 12, 14, 16. As a result, temperatures of the SMO films 20, 26, 32 may be maintained with less power. By using the cavity 78 instead of the multiple cavities 56, 58, 60, fabrication of the gas sensor device 10 is simplified. In addition, the cavity 78 provides a larger air gap for increased thermal insulation.

Figure 7:
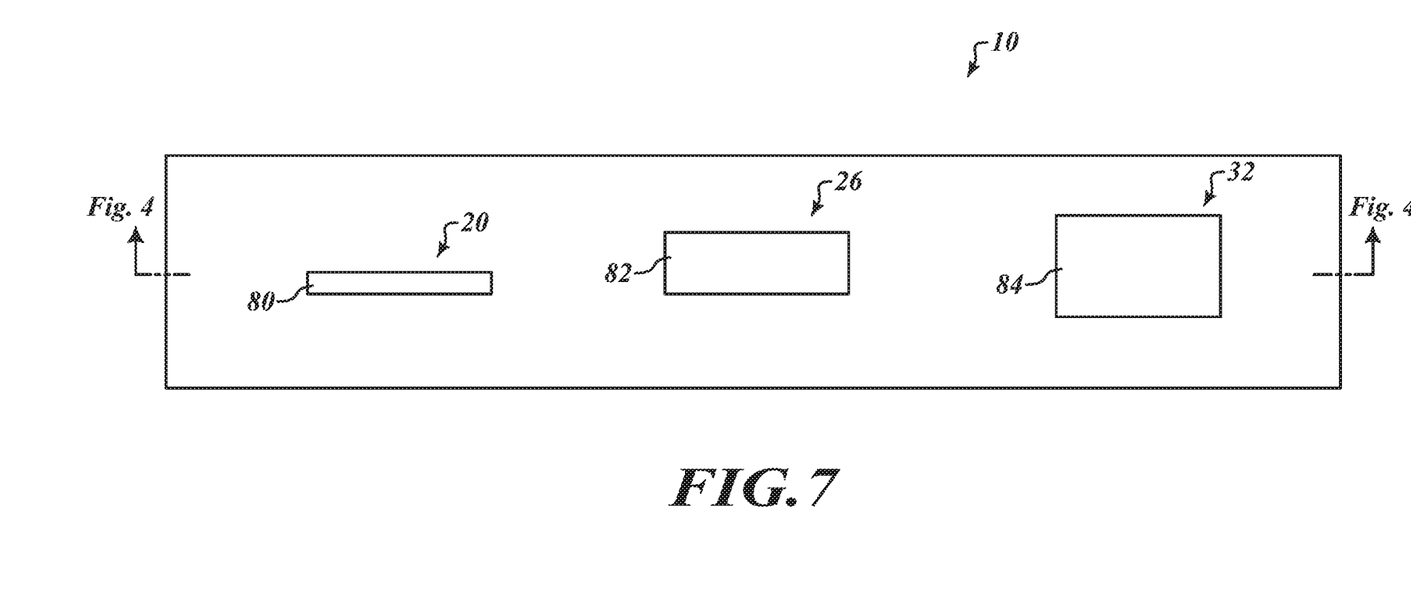
FIG. 7 is a top view of the gas sensor device according to another embodiment of the present disclosure.

FIG. 7 is a top view of the gas sensor device according to another embodiment of the present disclosure.

In the embodiment shown in FIG. 3, each of the SMO films 20, 26, 32 includes one or more SMO segments. For example, in the embodiment shown in FIG. 3, the SMO film 20 includes a single SMO segment 66, the SMO film 26 includes two separate SMO segment 68, 70, and the SMO film 32 includes three separate SMO segments 72, 74, 76. In contrast, in the embodiment shown in FIG. 7 each of the SMO films 20, 26, 32 includes a single SMO segment. For example, as shown in FIG. 7, the SMO film 20 includes an SMO segment 80, the SMO film 26 includes an SMO segment 82, and the SMO film 32 includes an SMO segment 84. Accordingly, fabrication of the gas sensor device 10 is simplified. In addition, the SMO films will consume less of the overall surface area of the gas sensor device 10.

Figure 8:
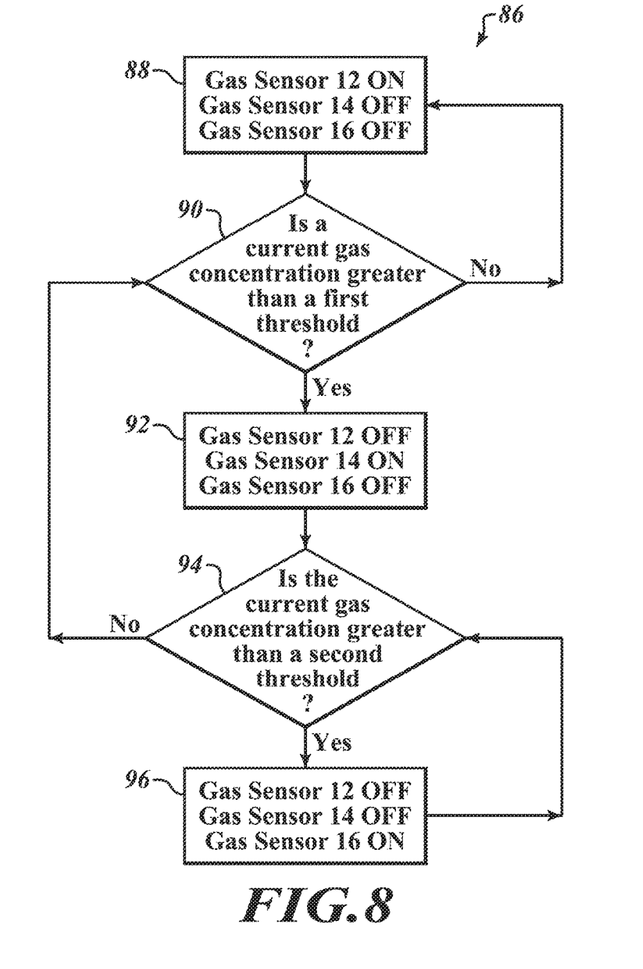
FIG. 8 is a flow diagram of a method of operating the gas sensor device according to an embodiment of the present disclosure.

FIG. 8 is a flow diagram of a method 86 of operating the gas sensor device 10 of FIG. 1 according to an embodiment of the present disclosure. The method 86 selectively activates and deactivates the gas sensors 12, 14, 16 based on a current gas concentration detected by the gas sensor device 10.

In block 88, the gas sensor 12 is ON, the gas sensor 14 is OFF, and the gas sensor 16 is OFF. In particular, the processor 18 activates the gas sensor 12, deactivates the gas sensor 14, and deactivates the gas sensor 16. When the gas sensor 12 is activated, the heater 22 is turned on to heat the SMO film 20 to a desired temperature. When the gas sensors 14, 16 are deactivated, the heaters 28, 34 are off.

As previously discussed, the SMO film 20 detects a low gas concentration range. Accordingly, in block 88, the gas sensor device 10 is configured to detect a low gas concentration range. For example, in the embodiment in which the SMO film 20 has a surface area approximately equal to 10 $\mu m^2$, the gas sensor device 10 is configured to detect gas concentrations in the range of 1 PPB to 1 PPM.

In decision branch 90, the processor 18 determines whether a current gas concentration detected by the gas sensor 12 is greater than a first threshold. If the current gas concentration is not greater than the first threshold, the method 86 returns to block 88. If the current gas concentration is greater than the first threshold, the method 86 moves to block 92.

In one embodiment, the first threshold is based on the surface area of the SMO film 20. The first threshold is set to be near or at an upper limit of the gas concentration range in which the SMO film 20 is sensitive to. For example, referring to FIG. 2, if the SMO film 20 has a surface area approximately equal to 10 $\mu m^2$, the first threshold may be set to 0.8 PPM.

In block 92, the gas sensor 12 is OFF, the gas sensor 14 is ON, and the gas sensor 16 is OFF. In particular, the processor 18 deactivates the gas sensor 12, activates the gas sensor 14, and deactivates the gas sensor 16. When the gas sensor 14 is activated, the heater 28 is turned on to heat the SMO film 26 to a desired temperature. When the gas sensors 12, 16 are deactivated, the heaters 22, 34 are off.

As previously discussed, the SMO film 26 detects a mid gas concentration range. Accordingly, in block 92, the gas sensor device 10 is configured to detect a mid gas concentration range. For example, in the embodiment in which the SMO film 26 has a surface area approximately equal to 100 $\mu m^2$, the gas sensor device 10 is configured to detect gas concentrations in the range of 1 PPM to 10 PPM.

In decision branch 94, the processor 18 determines whether the current gas concentration detected by the gas sensor 14 is greater than a second threshold. If the current gas concentration is not greater than the second threshold, the method 86 returns to block decision branch 90. If the current gas concentration is greater than the second threshold, the method 86 moves to block 96.

In one embodiment, the second threshold is based on the surface area of the SMO film 26. The second threshold is set to be near an upper limit of the gas concentration range in which the SMO film 26 is sensitive to. For example, referring to FIG. 2, if the SMO film 26 has a surface area approximately equal to 100 $\mu m^2$, the first threshold may be set to 8 PPM.

In block 96, the gas sensor 12 is OFF, the gas sensor 14 is OFF, and the gas sensor 16 is ON. In particular, the processor 18 deactivates the gas sensor 12, deactivates the gas sensor 14, and activates the gas sensor 16. When the gas sensor 16 is activated, the heater 34 is turned on to heat the SMO film 32 to a desired temperature. When the gas sensors 12, 14 are deactivated, the heaters 22, 28 are off.

As previously discussed, the SMO film 32 detects a high gas concentration range. Accordingly, in block 96, the gas sensor device 10 is configured to detect a high gas concentration range. For example, in the embodiment in which the SMO film 32 has a surface area approximately equal to 1000 $\mu m^2$, the gas sensor device 10 is configured to detect gas concentrations in the range of 10 PPM to 100 PPM. The method then returns to decision branch 94.

By selectively activating and deactivating the gas sensors 12, 14, 16 based on a current gas concentration detected by the gas sensor device 10, the gas sensor device 10 is able to obtain accurate readings for a wide range of concentration levels. In addition, the gas sensor device 10 conserves power, as the heaters 22, 28, 34 are turned on when appropriate, rather than being continuously turned on.

Figure 9:
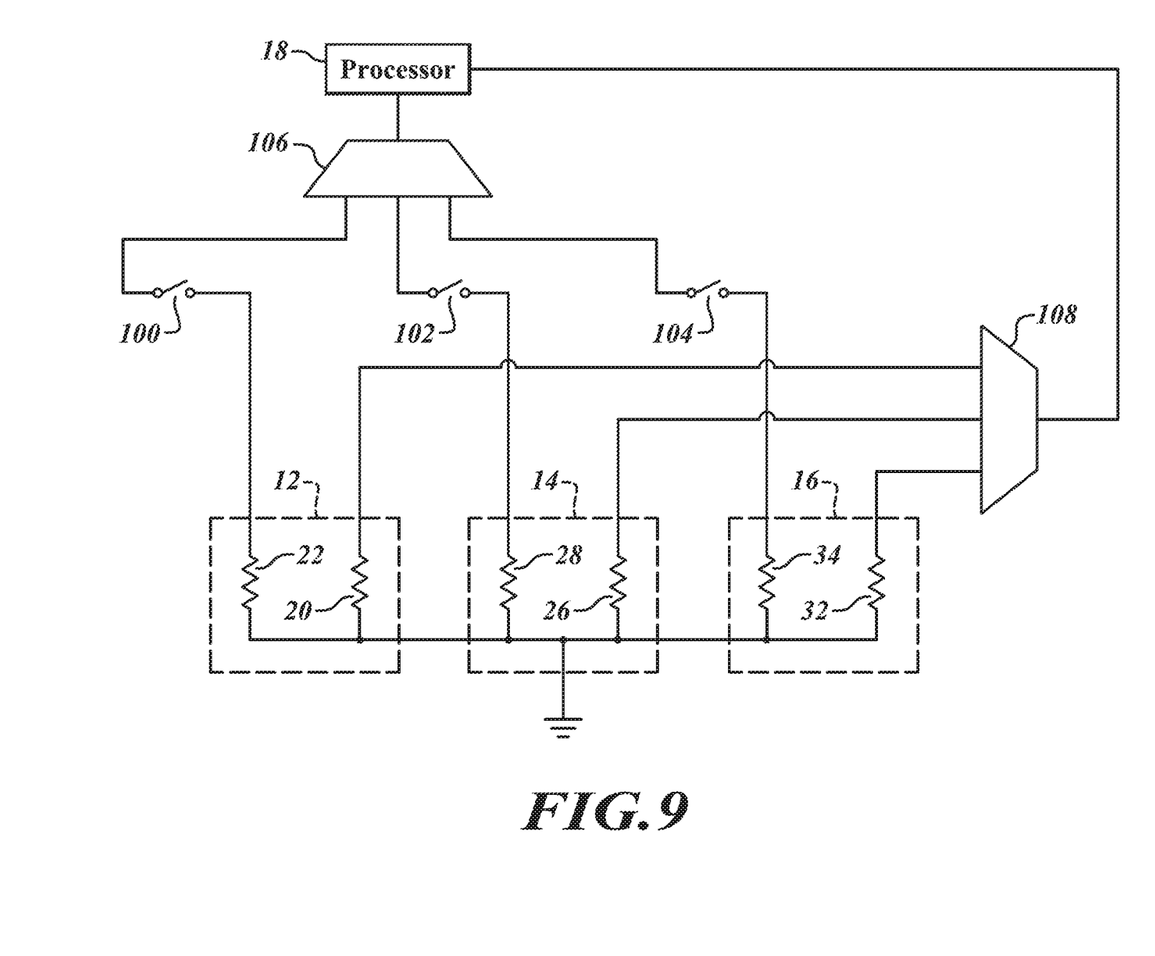
FIG. 9 is an electrical circuit representing the gas sensor device according to an embodiment of the present disclosure.

FIG. 9 is an electrical circuit representing the gas sensor device 10 according to an embodiment of the present disclosure.

The circuit includes the gas sensors 12, 14, 16; the processor 18; switches 100, 102, 104; and multiplexers 106, 108.

The SMO films 20, 26, 32 of the gas sensors 12, 14, 16 are electrically coupled to the multiplexer 108. Each of the SMO films 20, 26, 32 is represented as a resistive element. As previously discussed, each of the SMO films 20, 26, 32 acts as an active sensor area. When heated to certain temperatures, the SMO films 20, 26, 32 experience a change in resistivity when exposed to certain gases.

The heaters 22, 28, 34 of the gas sensors 12, 14, 16 are electrically coupled to the multiplexer 106 through the switches 100, 102, 104. Each of the heaters 22, 28, 34 is represented as a resistive element. As previously discussed, in one embodiment, the heaters 22, 28, 34 are resistive heaters that heat the SMO films 20, 26, 32 using the Joule effect by dissipating current through a resistance.

The processor 18 is electrically coupled to the multiplexers 106, 108. As previously discussed, the processor 18 is configured to activate and deactivate each of the gas sensors 12, 14, 16, measure current resistivity of the SMO films 20, 26, 32, and control the heaters 22, 28, 34 to heat the SMO films 20, 26, 32 to a particular temperature.

The switches 100, 102, 104 and the multiplexer 106 selectively activate and deactivate the heaters 22, 28, 34. For example, in block 88 of the method 86 shown in FIG. 8, the switch 100 is closed to activate the heater 22, and the multiplexer 106 electrically couples the heater 22 to the processor 18 such that the processor 18 may control the heater 22. Conversely, in block 88, the switches 102, 104 are opened to deactivate the heaters 28, 34, and the multiplexer 106 decouples the heaters 28, 34 from the processor 18.

The multiplexer 108 selectively couples the SMO films 20, 26, 32 to the processor 18 based on which of the gas sensors 12, 14, 16 are currently active, or ON. For example, in block 92 of the method 86 shown in FIG. 8, the multiplexer 108 electrically couples the SMO film 26 to the processor 18 such that a resistivity of the SMO film 26 may be measured and a gas concentration may be detected. Conversely, in block 92, the multiplexer 108 decouples the SMO films 20, 32 from the processor 18.

The various embodiments provide a gas sensor device that detects various species of gas including VOCs. The gas sensor device is able to obtain accurate readings for a wide range of concentration levels. Further, the gas sensor device has low power consumption and is ideal for portable devices.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   a substrate;
   a first gas sensor on the substrate, the first gas sensor including:

a first heater; and
a first semiconductor metal oxide (SMO) film on the first heater, the first SMO film having a first surface area, the first SMO film including a single segment, the first heater configured to heat the single segment of the first SMO film; and
a second gas sensor on the substrate, the second gas sensor including:
a second heater; and
a second SMO film on the second heater, the second SMO film having a second surface area that is greater than the first surface area, the second SMO film including a first segment and a second segment that is spaced from the first segment, the second heater configured to heat the first segment and the second segment of the second SMO film.

2. The device of claim 1, further comprising a processor configured to activate and deactivate the first gas sensor and the second gas sensor.

3. The device of claim 2 wherein the processor is configured to activate the second gas sensor in response to detection by the first gas sensor of a gas having a concentration that is greater than a first threshold.

4. The device of claim 1, further comprising:
a third gas sensor on the substrate, the third gas sensor including:
a third heater; and
a third SMO film on the third heater, the third SMO film having a third surface area that is greater than the second surface area, the third SMO film including a first segment, a second segment, and a third segment that are spaced from each other, the third heater configured to heat the first segment, the second segment, and the third segment of the third SMO film.

5. The device of claim 1 wherein the first gas sensor includes a first temperature sensor, and the second gas sensor includes a second temperature sensor.

6. A device, comprising:
a substrate;
a first heater on the substrate;
a first semiconductor metal oxide (SMO) film on the first heater, the first SMO film having a first surface area, the first SMO film including a single segment, the first heater configured to heat the single segment of the first SMO film;
a second heater on the substrate; and
a second SMO film on the second heater; the second SMO film having a second surface area that is greater than the first surface area, the second SMO film including a first segment and a second segment that is spaced from the first segment, the second heater configured to heat the first segment and the second segment of the second SMO film.

7. The device of claim 6, further comprising:
a first cavity, the first heater and the first SMO film overlying the first cavity; and
a second cavity, the second heater and the second SMO film overlying the second cavity.

8. The device of claim 6, further comprising:
a third heater on the substrate; and
a third SMO film on the third heater; the third SMO film having a third surface area that is greater than the second surface area, the third SMO film including a first segment, a second segment, and a third segment that are spaced from each other, the third heater configured to heat the first segment, the second segment, and the third segment of the third SMO film.

9. The device of claim 6, further comprising a processor configured to activate the second gas sensor in response to detection by the first gas sensor of a gas having a concentration that is greater than a first threshold.

10. The device of claim 6, further comprising:
a first temperature sensor on the substrate aligned with the first SMO film; and
a second temperature sensor on the substrate aligned with the second SMO film.

11. A device, comprising:
a first gas sensor including:
a first heater; and
a first gas sensitive film on the first heater, the first gas sensitive film having a first surface area, the first gas sensitive film including a single segment, the first heater configured to heat the single segment of the first gas sensitive film; and
a second gas sensor including:
a second heater; and
a second gas sensitive film on the second heater, the second gas sensitive film having a second surface area that is greater than the first surface area, the second gas sensitive film including a first segment and a second segment that is spaced from the first segment, the second heater configured to heat the first segment and the second segment of the second gas sensitive film.

12. The device of claim 11 wherein the first gas sensor is configured to detect gas concentrations in a first range, the second gas sensor is configured to detect gas concentrations in a second range, and the gas concentrations in the second range are larger than the gas concentrations in the first range.

13. The device of claim 11, further comprising:
a substrate;
a first dielectric layer on the substrate;
a second dielectric layer on the first dielectric layer;
a first cavity positioned between the first dielectric layer and the second dielectric layer, the first heater positioned on the second dielectric layer and directly overlying the first cavity; and
a second cavity positioned between the first dielectric layer and the second dielectric layer, the second heater positioned on the second dielectric layer and directly overlying the second cavity.

14. The device of claim 13, further comprising:
a third dielectric layer on the second dielectric layer, the first heater, and the second heater, the single segment of the first gas sensitive film and the first and second segments of the second gas sensitive film being on the third dielectric layer.

15. The device of claim 14, further comprising:
a fourth dielectric layer on the third dielectric layer, the fourth dielectric layer including openings that expose the single segment of the first gas sensitive film and the first and second segments of second gas sensitive film to a surrounding environment.

16. The device of claim 1 wherein the first gas sensor is configured to detect a gas species within a first concentration range, the second gas sensor is configured to detect the gas species within a second concentration range, and the second concentration range includes greater concentration levels than the first concentration range.

17. The device of claim 16 wherein the first heater is configured to heat the single segment of the first SMO film to a first temperature within a first temperature range, the second heater is configured to heat the first segment and the second segment of the second SMO film to a second temperature within a second temperature range, and the first temperature range overlaps the second temperature range.

18. The device of claim 1, further comprising:
a first dielectric layer on the first and second heaters, the single segment of the first SMO film and the first and second segments of the second SMO film being on the first dielectric layer.

19. The device of claim 18, further comprising:
a second dielectric layer on the first dielectric layer, the second dielectric layer including openings that expose the single segment of the first SMO film and the first and second segments of the second SMO film to a surrounding environment.

20. The device of claim 6 wherein the first heater is configured to heat the single segment of the first SMO film to a first temperature that is greater than a first threshold temperature and less than a second threshold temperature, the second heater is configured to heat the first segment and the second segment of the second SMO film to a second temperature that is greater than the first threshold temperature and less than the second threshold temperature.

* * * * *